(12) United States Patent
Bubenik et al.

(10) Patent No.: US 10,617,830 B2
(45) Date of Patent: Apr. 14, 2020

(54) HINGED SHIELD ASSEMBLIES AND RELATED METHODS

(71) Applicant: B. Braun Melsungen AG, Melsungen (DE)

(72) Inventors: Janko Bubenik, Melsungen (DE); Markus Dickel, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 11 days.

(21) Appl. No.: 16/030,738

(22) Filed: Jul. 9, 2018

(65) Prior Publication Data
US 2018/0318520 A1 Nov. 8, 2018

Related U.S. Application Data

(63) Continuation of application No. 14/662,678, filed on Mar. 19, 2015, now Pat. No. 10,029,049.

(51) Int. Cl.
*A61M 5/32* (2006.01)

(52) U.S. Cl.
CPC ........ *A61M 5/3202* (2013.01); *A61M 5/3216* (2013.01)

(58) Field of Classification Search
CPC .............. A61M 5/3216; A61M 5/3202; A61M 5/5086; A61M 25/0631
USPC ....................................................... 604/198
See application file for complete search history.

(56) References Cited

U.S. PATENT DOCUMENTS

| | | |
|---|---|---|
| 3,841,769 A | 10/1974 | Bowerman |
| 4,109,821 A | 8/1978 | Lutz |
| 4,620,813 A | 11/1986 | Lacher |
| 4,658,471 A | 4/1987 | Nakanishi |
| 4,886,503 A | 12/1989 | Miller |
| 4,982,842 A | 1/1991 | Hollister |
| 5,011,475 A | 4/1991 | Olson |
| 5,139,489 A | 8/1992 | Hollister |
| 5,154,285 A | 10/1992 | Hollister |
| 5,232,454 A | 8/1993 | Hollister |
| 5,232,455 A | 8/1993 | Hollister |
| 5,277,311 A | 1/1994 | Hollister |

(Continued)

FOREIGN PATENT DOCUMENTS

| | | |
|---|---|---|
| CN | 1411874 A | 4/2003 |
| CN | 2763429 Y | 3/2006 |

(Continued)

OTHER PUBLICATIONS

English translation of an Office Action including search report on corresponding foreign application (BR Application No. BR112013012582-9) from the Brazilian Patent Office dated Aug. 1, 2019.

(Continued)

*Primary Examiner* — Phillip A Gray
(74) *Attorney, Agent, or Firm* — Klein, O'Neill & Singh, LLP

(57) ABSTRACT

Embodiments of the shield assemblies include a shield that is pivotably secured to a needle hub. A ball-and-socket hinge secures the shield and the hub to one another. The assembly includes a reversible shield lock to hold the shield in the needle-protected position. The assembly further includes at least one stop piece to stop the shield from over-rotating.

26 Claims, 9 Drawing Sheets

(56) References Cited

U.S. PATENT DOCUMENTS

| | | | |
|---|---|---|---|
| 5,312,368 A | 5/1994 | Haynes | |
| 5,370,628 A | 12/1994 | Allison et al. | |
| 5,385,551 A | 1/1995 | Shaw | |
| 5,389,076 A | 2/1995 | Shaw | |
| 5,419,766 A | 5/1995 | Chang et al. | |
| 5,423,758 A | 6/1995 | Shaw | |
| 5,423,765 A | 6/1995 | Hollister | |
| 5,423,766 A | 6/1995 | Di Cesare | |
| 5,433,711 A | 7/1995 | Balaban et al. | |
| 5,447,501 A | 9/1995 | Karlsson et al. | |
| 5,466,223 A | 11/1995 | Bressler et al. | |
| 5,486,163 A | 1/1996 | Haynes | |
| 5,487,733 A | 1/1996 | Caizza et al. | |
| 5,490,841 A | 2/1996 | Landis | |
| 5,509,907 A | 4/1996 | Bevilacqua | |
| 5,533,974 A | 7/1996 | Gaba | |
| 5,536,257 A | 7/1996 | Byrne et al. | |
| 5,559,318 A | 9/1996 | Aoki | |
| 5,584,816 A | 12/1996 | Gyure et al. | |
| 5,588,767 A | 12/1996 | Merlo | |
| 5,599,313 A | 2/1997 | Gyure et al. | |
| 5,599,318 A | 2/1997 | Sweeney et al. | |
| 5,603,699 A | 2/1997 | Shine | |
| 5,615,771 A | 4/1997 | Hollister | |
| 5,632,732 A | 5/1997 | Szabo et al. | |
| 5,643,219 A | 7/1997 | Burns | |
| 5,649,622 A | 7/1997 | Hollister | |
| 5,662,617 A | 9/1997 | Odell et al. | |
| 5,669,889 A | 9/1997 | Gyure et al. | |
| 5,681,295 A | 10/1997 | Gyure et al. | |
| 5,693,022 A | 12/1997 | Haynes | |
| 5,704,920 A | 1/1998 | Gyure | |
| 5,733,265 A | 3/1998 | Bachman et al. | |
| 5,743,888 A | 4/1998 | Wilkes et al. | |
| 5,746,726 A * | 5/1998 | Sweeney | A61M 5/3216 604/192 |
| 5,807,351 A | 9/1998 | Kashmer | |
| 5,810,775 A | 9/1998 | Shaw | |
| 5,823,997 A | 10/1998 | Thorne | |
| 5,836,920 A | 11/1998 | Robertson | |
| 5,868,716 A | 2/1999 | Sweeney et al. | |
| 5,885,249 A | 3/1999 | Irisawa | |
| 5,891,103 A | 4/1999 | Burns | |
| 5,913,846 A | 6/1999 | Szabo | |
| 5,919,165 A | 7/1999 | Benson | |
| 5,957,892 A | 9/1999 | Thorne | |
| 5,980,488 A | 11/1999 | Thorne | |
| RE36,447 E | 12/1999 | Byrne et al. | |
| 6,042,570 A | 3/2000 | Bell et al. | |
| 6,096,024 A | 8/2000 | Graves et al. | |
| 6,120,480 A | 9/2000 | Zhang et al. | |
| 6,149,629 A | 11/2000 | Wilson et al. | |
| RE37,110 E | 3/2001 | Hollister | |
| RE37,252 E | 7/2001 | Hollister | |
| 6,254,575 B1 | 7/2001 | Thorne, Jr. et al. | |
| 6,280,420 B1 | 8/2001 | Ferguson et al. | |
| 6,298,541 B1 * | 10/2001 | Newby | A61M 5/3216 29/451 |
| 6,319,232 B1 | 11/2001 | Kashmer | |
| 6,328,713 B1 | 12/2001 | Hollister | |
| 6,334,857 B1 | 1/2002 | Hollister et al. | |
| 6,355,021 B1 | 3/2002 | Nielsen et al. | |
| 6,436,086 B1 | 8/2002 | Newby et al. | |
| 6,440,104 B1 | 8/2002 | Newby et al. | |
| 6,517,522 B1 | 2/2003 | Bell et al. | |
| 6,524,281 B1 | 2/2003 | Hudon | |
| 6,551,287 B2 | 4/2003 | Hollister et al. | |
| 6,561,476 B2 | 5/2003 | Carnevali | |
| 6,582,397 B2 | 6/2003 | Alesi et al. | |
| 6,592,556 B1 | 7/2003 | Thorne | |
| 6,616,638 B2 | 9/2003 | Peters, III | |
| 6,635,032 B2 | 10/2003 | Ward, Jr. | |
| 6,648,855 B2 | 11/2003 | Crawford et al. | |
| 6,699,217 B2 | 3/2004 | Bennett et al. | |
| 6,719,737 B2 | 4/2004 | Kobayashi | |
| 6,752,788 B2 | 6/2004 | Tuen | |
| 6,780,169 B2 | 8/2004 | Crawford | |
| 6,811,547 B2 | 11/2004 | Wilkinson | |
| 6,824,531 B1 | 11/2004 | Zecha, Jr. et al. | |
| 6,840,922 B2 | 1/2005 | Nielsen et al. | |
| 6,869,418 B2 | 3/2005 | Marano-Ford | |
| D505,200 S | 5/2005 | Simpson et al. | |
| 6,918,891 B2 | 7/2005 | Bressler et al. | |
| 6,921,388 B2 | 7/2005 | Swenson | |
| 6,951,551 B2 | 10/2005 | Hudon | |
| 7,001,363 B2 | 2/2006 | Ferguson et al. | |
| RE39,107 E | 5/2006 | Shaw | |
| 7,112,190 B2 | 9/2006 | Bressler et al. | |
| 7,128,726 B2 | 10/2006 | Crawford et al. | |
| 7,147,623 B2 | 12/2006 | Mathiasen | |
| 7,163,526 B2 | 1/2007 | Leong et al. | |
| 7,186,240 B1 | 3/2007 | Kronja | |
| 7,198,618 B2 | 4/2007 | Ferguson et al. | |
| 7,201,736 B2 | 4/2007 | Hauri | |
| 7,220,249 B2 | 5/2007 | Hwang et al. | |
| 7,223,258 B2 | 5/2007 | Crawford | |
| 7,250,038 B2 | 7/2007 | Simpson et al. | |
| 7,316,668 B2 | 1/2008 | Swenson | |
| 7,322,963 B2 | 1/2008 | Goh | |
| 7,361,159 B2 | 4/2008 | Fiser et al. | |
| 7,387,615 B2 | 6/2008 | Coelho et al. | |
| 7,413,560 B2 | 8/2008 | Chong et al. | |
| 7,488,306 B2 | 2/2009 | Nguyen | |
| 7,537,581 B2 | 5/2009 | Hwang | |
| 7,553,296 B2 | 6/2009 | Bedford et al. | |
| 7,591,800 B2 | 9/2009 | Nguyen | |
| 7,632,252 B2 | 12/2009 | Prais et al. | |
| 7,635,352 B2 | 12/2009 | Adams | |
| 7,648,480 B2 | 1/2010 | Bosel et al. | |
| 7,717,877 B2 | 5/2010 | Lavi et al. | |
| 7,722,572 B2 | 5/2010 | Sprinkle et al. | |
| 7,803,138 B2 | 9/2010 | Bressler et al. | |
| 7,811,261 B2 | 10/2010 | Rubinstein et al. | |
| 7,833,198 B2 | 11/2010 | Bressler et al. | |
| 7,854,723 B2 | 12/2010 | Hwang et al. | |
| 7,862,547 B2 | 1/2011 | Ferguson et al. | |
| 7,871,397 B2 | 1/2011 | Schraga | |
| 7,938,800 B2 | 5/2011 | Koh | |
| 7,951,090 B2 | 5/2011 | Sarstedt | |
| 7,967,794 B2 | 6/2011 | Bosel et al. | |
| 8,016,796 B2 | 9/2011 | Simas, Jr. et al. | |
| 8,029,463 B2 | 10/2011 | Hauri | |
| 8,038,654 B2 | 10/2011 | Lim et al. | |
| 8,057,431 B2 | 11/2011 | Woehr et al. | |
| 8,061,007 B2 | 11/2011 | Simpson et al. | |
| 8,100,858 B2 | 1/2012 | Woehr et al. | |
| 8,109,910 B2 | 2/2012 | Zastawny et al. | |
| 8,152,761 B2 | 4/2012 | Hauri et al. | |
| 8,162,882 B2 | 4/2012 | Rubinstein et al. | |
| 8,167,851 B2 | 5/2012 | Sen | |
| 8,172,809 B2 | 5/2012 | Ferguson et al. | |
| 8,177,063 B1 | 5/2012 | Simm et al. | |
| 8,182,451 B2 | 5/2012 | Bressler et al. | |
| 8,226,576 B2 | 7/2012 | Swenson et al. | |
| 8,226,604 B2 | 7/2012 | Madin et al. | |
| 8,226,617 B2 | 7/2012 | Ferguson et al. | |
| 8,231,583 B2 | 7/2012 | Swenson | |
| 8,251,961 B2 | 8/2012 | Hauri et al. | |
| 8,277,408 B2 | 10/2012 | Crawfprd et al. | |
| 8,287,498 B2 | 10/2012 | Tan et al. | |
| 8,425,472 B2 | 4/2013 | Bressler et al. | |
| 8,608,695 B2 | 12/2013 | Hauri et al. | |
| 8,622,960 B2 | 1/2014 | Madin et al. | |
| 8,641,680 B2 | 2/2014 | Simas, Jr. | |
| 8,708,977 B2 | 4/2014 | Bressler et al. | |
| 8,827,955 B2 | 9/2014 | Haindl et al. | |
| 2002/0062107 A1 | 5/2002 | Parmigiani et al. | |
| 2002/0072715 A1 | 6/2002 | Newby et al. | |
| 2003/0060773 A1 | 3/2003 | Nguyen | |
| 2003/0078548 A1 | 4/2003 | Kobayashi | |
| 2003/0125676 A1 | 7/2003 | Swenson et al. | |
| 2003/0181860 A1 | 9/2003 | Swenson | |
| 2003/0181868 A1 | 9/2003 | Swenson | |
| 2003/0187398 A1 | 10/2003 | Crawford | |

(56) References Cited

U.S. PATENT DOCUMENTS

| | | |
|---|---|---|
| 2003/0187399 A1 | 10/2003 | Crawford |
| 2003/0191438 A1 | 10/2003 | Ferguson et al. |
| 2003/0220618 A1 | 11/2003 | Crawford |
| 2004/0044318 A1 | 3/2004 | Fiser et al. |
| 2004/0054334 A1 | 3/2004 | Prais et al. |
| 2004/0059302 A1 | 3/2004 | Crawford et al. |
| 2004/0078007 A1 | 4/2004 | Nguyen |
| 2005/0004531 A1 | 1/2005 | Hwang et al. |
| 2005/0065481 A1 | 3/2005 | Hauri et al. |
| 2005/0124944 A1 | 6/2005 | Hwang |
| 2005/0146081 A1 | 7/2005 | MacLean et al. |
| 2006/0052748 A1 | 3/2006 | Coelho et al. |
| 2006/0149188 A1 | 7/2006 | Simas, Jr. |
| 2006/0200078 A1 | 9/2006 | Konrad |
| 2006/0224122 A1 | 10/2006 | Bosel et al. |
| 2006/0270947 A1 | 11/2006 | Crawford et al. |
| 2006/0270979 A1 | 11/2006 | Simas, Jr. et al. |
| 2007/0088261 A1 | 4/2007 | Lew et al. |
| 2007/0156088 A1 | 7/2007 | Hauri |
| 2007/0274770 A1 | 11/2007 | Sagisaka et al. |
| 2008/0208138 A1 | 8/2008 | Lim et al. |
| 2008/0306451 A1 | 12/2008 | Woehr et al. |
| 2009/0173330 A1 | 7/2009 | Akins |
| 2011/0288496 A1 | 11/2011 | Harms et al. |
| 2011/0301546 A1 | 12/2011 | Harms et al. |
| 2013/0237927 A1 | 9/2013 | Sim et al. |
| 2013/0274684 A1 | 10/2013 | Bubenik et al. |
| 2013/0331793 A1 | 12/2013 | Gonzales et al. |
| 2014/0052072 A1 | 2/2014 | Simas, Jr. et al. |
| 2014/0135713 A1 | 5/2014 | Domonkos |

FOREIGN PATENT DOCUMENTS

| | | |
|---|---|---|
| DE | 69722333 T2 | 3/2004 |
| EP | 0433250 A2 | 6/1991 |
| EP | 1380315 A1 | 1/2004 |
| FR | 2640674 A | 6/1990 |
| JP | 11-124158 A | 5/1999 |
| JP | H 11-299692 | 11/1999 |
| JP | 2002 102344 A | 4/2002 |
| JP | 2004-525741 A | 8/2004 |
| JP | 2005-521537 A | 7/2005 |
| JP | 2006-183709 A | 7/2006 |
| JP | 2009-513301 A | 4/2009 |
| JP | 2013-545548 A | 12/2013 |
| JP | 2014-520590 A | 8/2014 |
| WO | WO 2006/041442 | 4/2006 |
| WO | WO 2008/076459 A1 | 6/2008 |
| WO | WO 2010/059345 A2 | 5/2010 |
| WO | WO 2012/071400 A2 | 5/2012 |
| WO | 2012/111560 A1 | 8/2012 |
| WO | 2012/152207 A1 | 11/2012 |
| WO | WO 2013006134 | 1/2013 |
| WO | WO 2013134498 | 9/2013 |

OTHER PUBLICATIONS

Examination Report on corresponding foreign application (EP Application No. 16712002.1) from the European Patent Office dated Aug. 3, 2018.
International Search Report and Written Opinion on corresponding PCT application (PCT/US2011/061825) from International Searching Authority (KR) dated Jun. 29, 2012.
International Search Report and Written Opinion on corresponding PCT application (PCT/EP2016/055715) from International Searching Authority (EPO) dated May 17, 2016.
International Preliminary Report on Patentability on corresponding PCT application (PCT/EP2016/055715) from International Searching Authority (EPO) dated Sep. 28, 2017.
Examiner's Report on corresponding foreign application (CN Application No. 201180056060.X) from State Intellectual Property Office dated Sep. 29, 2014.
Examiner's Report on corresponding foreign application (CN Application No. 201180056060.X) from State Intellectual Property Office dated Jan. 4, 2016.
Decision of Reexamination on corresponding foreign application (CN Application No. 201180056060.X) from State Intellectual Property Office dated Nov. 24, 2017.
Office Action on corresponding foreign application (DE Application No. 11 2011 103 856.9) from the German Patent Office dated Feb. 20, 2018.
Examiner's Report on corresponding foreign application (JP Application No. 2013-541017) from the Japan Patent Office dated Oct. 20, 2015.
Office Action on corresponding foreign application (RU Application No. 2013128474) from the Russian Patent Office dated Apr. 30, 2015.
Decision on Grant on corresponding foreign application (RU Application No. 2013128474) from the Russian Patent Office dated Jan. 13, 2016.
Office Action from related US application (U.S. Appl. No. 13/878,305) dated Feb. 26, 2015.
Final Office Action from related US application (U.S. Appl. No. 13/878,305) dated Jun. 18, 2015.
Non-Final Office Action from related US application (U.S. Appl. No. 13/878,305) dated Feb. 11, 2016.
Non-Final Office Action from related US application (U.S. Appl. No. 13/878,305) dated Aug. 4, 2016.
Non-Final Office Action from related US application (U.S. Appl. No. 13/878,305) dated Apr. 4, 2017.
Office Action on corresponding foreign application (CN Application No. 201180056060.X) from State Intellectual Property Office dated Jun. 19, 2015.
Rejection Decision on corresponding foreign application (CN Application No. 201180056060.X) from State Intellectual Property Office dated Jul. 25, 2016.
Notification of Reexamination on corresponding foreign application (CN Application No. 201180056060.X) from State Intellectual Property Office dated May 25, 2017.
Office Action on corresponding foreign application (JP Application No. 2013-541017) from the Japan Patent Office dated Aug. 2, 2016.
Office Action on corresponding foreign application (RU Application No. 2013128474) from the Russian Patent Office dated Sep. 15, 2015.
Non-Final Office Action from related US application (U.S. Appl. No. 13/878,305) dated Dec. 1, 2014.
Final Office Action from related US application (U.S. Appl. No. 13/878,305) dated Sep. 25, 2015.
Non-Final Office Action on corresponding US application (U.S. Appl. No. 14/662,678) dated Apr. 6, 2017.
Final Office Action on corresponding US application (U.S. Appl. No. 14/662,678) dated Oct. 19, 2017.
Notice of Allowance on corresponding US application (U.S. Appl. No. 14/662,678) dated Mar. 21, 2018.
Office Action on corresponding foreign application (AU Application No. 2016232180) from the Australian Patent Office dated Oct. 14, 2019.
Office Action on corresponding foreign application (EP Application No. 16712002.1) from the Australian Patent Office dated Oct. 30, 2019.
Office Action on corresponding foreign application (JP Application No. 2017-540613) from the Japan Patent Office dated Jan. 21, 2020.

* cited by examiner

HINGED SHIELD ASSEMBLIES AND RELATED METHODS

FIELD

Shields for needle devices are generally discussed herein with hinged shield devices for use with hypodermic needles more particularly discussed.

BACKGROUND

Recapping is a common procedure for periods between drawing up fluids into a syringe and administering injections through a needle. The recapping procedure can occasionally cause needlesticks since users sometime misalign the needles with the openings on the caps. Injuries can also occur after an injection and prior to the discarding of the needles. Needlesticks can be painful, but can also cause great inconvenience because all needlesticks must be reported. Also, since needles related to needlesticks must be discarded, medications contained within the syringes are unnecessarily wasted. Furthermore, fluids linked to these "clean" type of needlesticks can cause injuries and adverse reactions.

Additionally, needles may be damaged by over-rotation of caps during recapping. A damaged needle may be shifted from its normal orientation, causing the tip to stick out from under the cap. This leads to the same dangers of needlesticks outlined above.

SUMMARY

Aspects the present device, system, and method include a needle shield 108 hingedly connected to a needle hub 106, such as by way of a ball-and-socket hinge 144. At least one stop piece 190 is positioned on the needle hub 106 to abut the shield to then stop the shield from over rotating along one rotational directional when the shield is in a closed position over a needle 104 attached to the needle hub 106. The needle hub 106 can include a flange 162 and two stop pieces 190 located on the flange 162 to stop the shield from over rotating. The stop pieces 190 can each include a base 207 or a combination base 207 and a capture element 198 to define a retention space 209. The two capture elements 198 can be configured to prevent the first and second sidewalls 110, 112 of the shield 108 from spreading or expanding radially of the lengthwise axis of the needle beyond the width of the two stop pieces 190.

In an example, a hinged shield assembly 100 is provided. The hinged shield assembly 100 can comprise: a needle hub 106 including a first hinge part 500, a needle 104 extending from the needle hub 106 and comprising a lengthwise axis; a shield 108 including a second hinge part 502 that engages the first hinge part 500 to pivotably secure the shield 108 to the hub 106, the shield 108 further including a plurality of sidewalls 110, 112, 114 that partially surround the needle 104 when the shield 106 is in a protected position; wherein each of the sidewalls 110, 112, 114 comprises a base end 116; and at least one stop piece 190 extending radially of the lengthwise axis from the needle hub 106 and located in a rotational path of the shield 108 such that at least one of the plurality of sidewalls 110, 112, 114 contacts the at least one stop piece 190 to prevent over rotation of the base end 116 of each of the sidewalls 110, 112, 114 beyond an at rest point upon contact with the at least one stop piece 190 in one rotational direction when the shield 108 is in the protected position.

The hinged shield assembly 100, wherein the at least one stop piece 190 can comprise a base 207 having a radially extending planar surface to abut the shield 108.

The hinged shield assembly 100 can further comprise a capture element 198 extending from the base 207 in an axial direction to define a retention space 209.

The hinged shield assembly 100 can further comprise a reduced depth portion 197 formed on at least one of the plurality of sidewalls 110, 112, 114 on a side of the hinged shield assembly corresponding to the at least one stop piece 190.

The hinged shield assembly 100 can further comprise at least one tab 136 formed on at least one of the plurality of sidewalls 110, 112, 114 for engaging the needle hub 106 in the protected position.

The hinged shield assembly 100 can further comprise at least one notch 174 formed on the needle hub 106 for receiving the at least one tab 136 in the protected position.

The hinged shield assembly 100 wherein one of the plurality of sidewalls 110, 112, 114 can be a central sidewall 114 and wherein a hook 130 can be formed with the central sidewall 114. The hook 130 can hook onto the needle 104 or a cylinder post 280 holding the needle 104 in a protected position.

The hinged shield assembly 100 wherein the first hinge part 500 can comprise sockets 142.

The hinged shield assembly 100 wherein the second hinge part 502 can comprise balls 134.

The hinged shield assembly 100 can further comprise a second stop piece 190 comprising a base 207 and wherein two bases 207 on the needle hub 106 can define a stop width.

The hinge shield assembly 100 wherein a first sidewall 110 and a second sidewall 112 of the plurality of sidewalls 110, 112, 114 can define a shield width and wherein the stop width can wider than the shield width, equal to the shield width, or smaller than the shield width.

The hinge shield assembly 100, wherein the first sidewall 110 and the central wall 114 can include a slit 124 to enable a base end 116 of the first sidewall 110 to defect relative to the central wall 114.

The hinge shield assembly 100, wherein the second sidewall 112 and the central wall 114 can include a slit 124 to enable a base end 116 of the second sidewall 112 to defect relative to the central wall 114.

The hinge shield assembly 100 wherein the at least one stop piece 190 can be located on a transverse base 150 defining a flange 162, which can intersect an elongated portion 148 on the needle hub 106 between a distal cylindrical portion 154 and a proximal cylindrical portion 152.

The hinge shield assembly 100 wherein the flange 162 can include a first edge, a second edge, and a first side edge and wherein the at least one stop piece 190 can be located on the side edge 146a, between the first edge and the second edge.

The hinge shield assembly 100 wherein flange 162 can include an upper surface facing the distal cylindrical portion 154, and wherein the radially extending planar surface of the base 207 can be offset from the upper surface.

The hinge shield assembly 100 can further comprise a second stop piece 190 having a base 207 with a radially extending planar surface to abut the shield 108 located on a second side 146a of the flange 162.

The hinge shield assembly 100 wherein the flange 162 can include an upper surface facing the distal cylindrical portion 154, and wherein the radially extending planar surfaces of the two bases 207 can be offset from the upper surface.

The hinge shield assembly 100, wherein the flange 162 can include an upper surface facing the distal cylindrical portion 154, and wherein the radially extending planar surfaces of the two bases 207 can be co-planar with the upper surface.

The hinge shield assembly 100 wherein a notch 174 can be located at the first edge and the first hinge part 500 can be located at the second edge.

The hinge shield assembly 100 can further comprise a plurality of fins 160 formed on the distal cylindrical portion 154.

The hinge shield assembly 100 wherein the first hinge part 500 can comprise two sockets 142 each with a perimeter defining an opening 168 having an opening diameter.

The hinge shield assembly 100 wherein the second hinge part 502 can comprise a pair of balls 134 fitted into the two sockets 142.

The hinge shield assembly 100 can further comprise a capture element 198 extending from each of the base 207.

The hinge shield assembly 100 wherein the two bases 207 can define radially extending members and the capture elements 198 can define axially extending members.

The hinge shield assembly 100 wherein each pair of base 207 and capture element 198 can form a generally "L" shape structure when viewing from an end.

The hinge shield assembly 100 wherein the capture elements 198 can contact a ledge on a reduced depth portion 197 on a respective sidewall 110, 112.

Further aspects of the disclosed hinged shield assembly 100 can comprise: a needle hub 106 including a flange 162 and a first hinge part 500 formed with the flange 162, a needle 104 extending from the needle hub 106 and comprising a lengthwise axis; a shield 108 including a second hinge part 502 that engages the first hinge part 500 to pivotably secure the shield 108 to the hub 106, the shield 108 further including a plurality of sidewalls 110, 112, 114 that partially surround the needle 104 when the shield 106 is in a protected position; wherein each of the sidewalls 110, 112, 114 comprises a base end 116; and two stop pieces 190 extending from the flange 162 radially of the lengthwise axis and located in a rotational path of the shield 108 such that a first sidewall 110 and a second sidewall 112 of the plurality of walls 110, 112, 114 contact the two stop pieces 190 to prevent over rotation of the base end 116 of the first and second sidewalls 110, 112 beyond an at rest point upon contact with the two stop pieces 190 in one rotational direction when the shield 108 is the protected position.

The hinged shield assembly 100 wherein each stop piece 190 can include a base 207 and a capture element 198 extending from the base 207 in an axial direction to define a retention space 209.

The hinged shield assembly 100 wherein at least a portion of the base end 116 of the first sidewall 110 and at least a portion of the base end 116 of the second sidewall 112 can both be located in the two retention spaces 209.

The hinged shield assembly 100 wherein the base end 116 of the first sidewall 110 and the base end 116 of the second sidewall 112 can each comprise a reduced depth portion 197 and wherein the reduced depth portion 197 can be located in a respective retention space 209.

The hinged shield assembly 100 can further comprise a tab 136 on each of the first and second sidewalls 110, 112 for engaging the needle hub 106 in the protected position.

The hinged shield assembly 100 can further comprise two notches 174 formed on the needle hub 106 for receiving the two tabs 136 in the protected position.

The hinged shield assembly 100 wherein the two stop pieces 190 can define a stop width.

The hinge shield assembly 100 wherein the first sidewall 110 and the second sidewall 112 of the plurality of sidewalls 110, 112, 114 can define a shield width and wherein the stop width can be wider than the shield width, equal to the shield width, or less than the shield width.

The hinge shield assembly 100 wherein the flange 162 can include a first edge, a second edge, a first side edge 146a, a second side edge 146a, and wherein the two stop pieces 190 can be located, one each, on the first side edge 146a and the second side edge 146a between the first edge and the second edge.

A further aspect of the present disclosure includes a method of manufacturing a hinge shield assembly 100. The method can comprise: forming a needle hub 106 including a flange 162 and a first hinge part 500 formed with the flange 162; extending a needle 104 from the needle hub 106, said needle comprising a lengthwise axis; forming a shield 108 including a second hinge part 502 that engages the first hinge part 500 to pivotably secure the shield 108 to the hub 106, the shield 108 further including a plurality of sidewalls 110, 112, 114 that partially surround the needle 104 when the shield 106 is in a protected position; wherein each of the sidewalls 110, 112, 114 comprises a base end 116; and forming two stop pieces 190 extending from the flange 162 radially of the lengthwise axis and positioning the two stop pieces 190 in a rotational path of the shield 108 such that a first sidewall 110 and a second sidewall 112 of the plurality of walls 110, 112, 114 contact the two stop pieces 190 to prevent over rotation of the base end 116 of the first and second sidewalls 110, 112 beyond an at rest point upon contact with the two stop pieces 190 in one rotational direction when the shield 108 is the protected position.

A further aspect of the present disclosure includes a method of using a hinge shield assembly 100 described elsewhere herein.

Yet another aspect of the present disclosure can include a hinge shield assembly 100 comprising a needle hub 106 having two sockets 142 or two spaced apart balls 134 and a shield 108 having at least three walls 110, 112, 114 defining an interior space for covering a needle 104, and the other one of the two sockets 142 or two spaced apart balls 134 located on the shield 108; and wherein two stop pieces 190 are formed with the needle hub 106 and arranged on the needle hub 106 to stop two of the sidewalls 110, 112, 114 from rotating along a rotational direction when the shield 108 moves over the needle 104 in a protective position and wherein the two spaced apart balls 134 are located in the two socket 142.

BRIEF DESCRIPTION OF THE DRAWINGS

The various embodiments of the present hinged shield assemblies now will be discussed in detail with an emphasis on highlighting the advantageous features. These embodiments depict the novel and non-obvious hinged shield assemblies shown in the accompanying drawings, which are for illustrative purposes only. These drawings include the following figures, in which like numerals indicate like parts.

DETAILED DESCRIPTION

Figure 1:
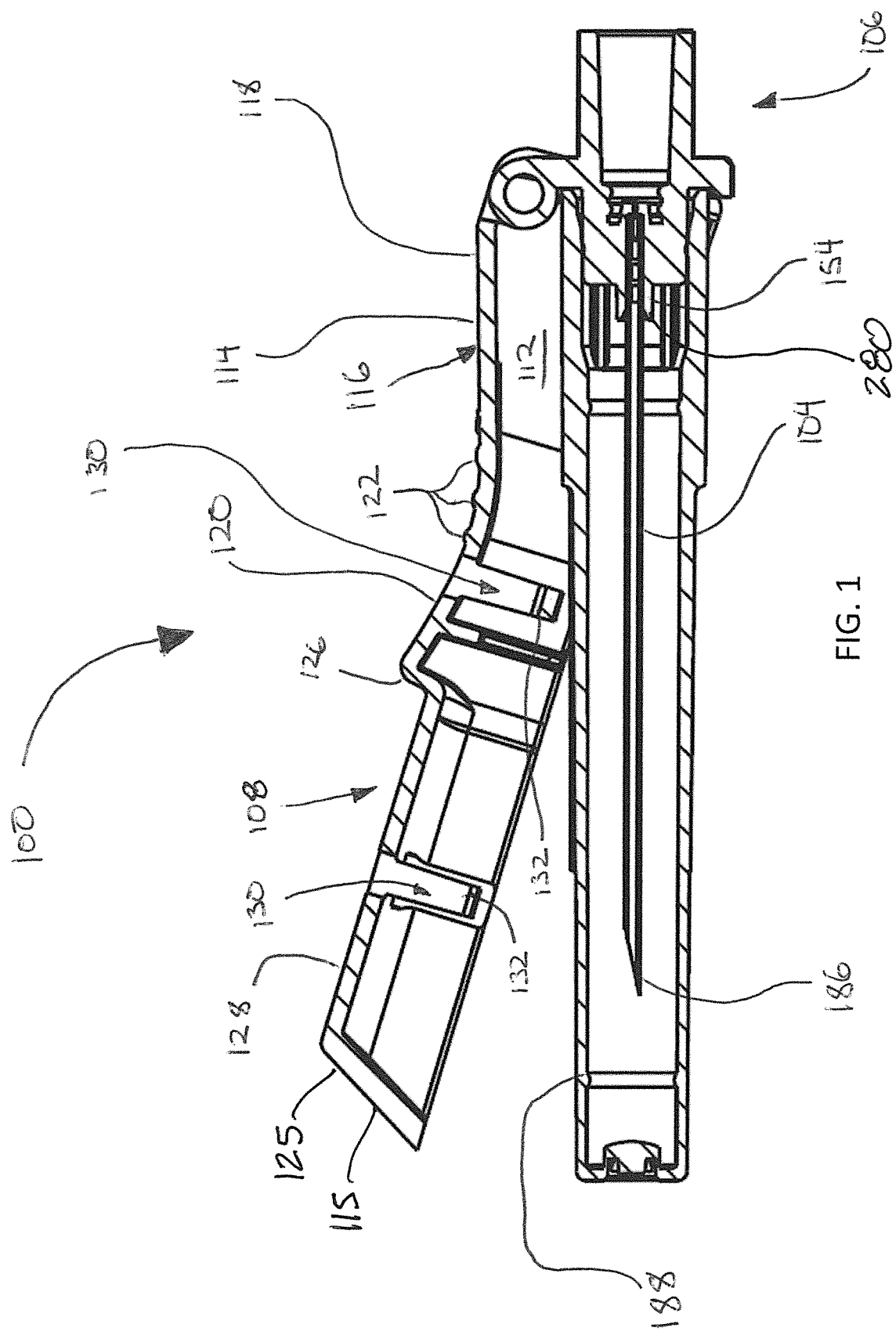
FIG. 1 is a side cross sectional view of a hinged needle assembly in a packaged position with a removable cap.

The following detailed description describes the present embodiments, including apparatuses, devices, and methods, with reference to the drawings. In the drawings, reference numbers label elements of the present embodiments. These reference numbers are reproduced below in connection with the discussion of the corresponding drawing features.

Figure 2:
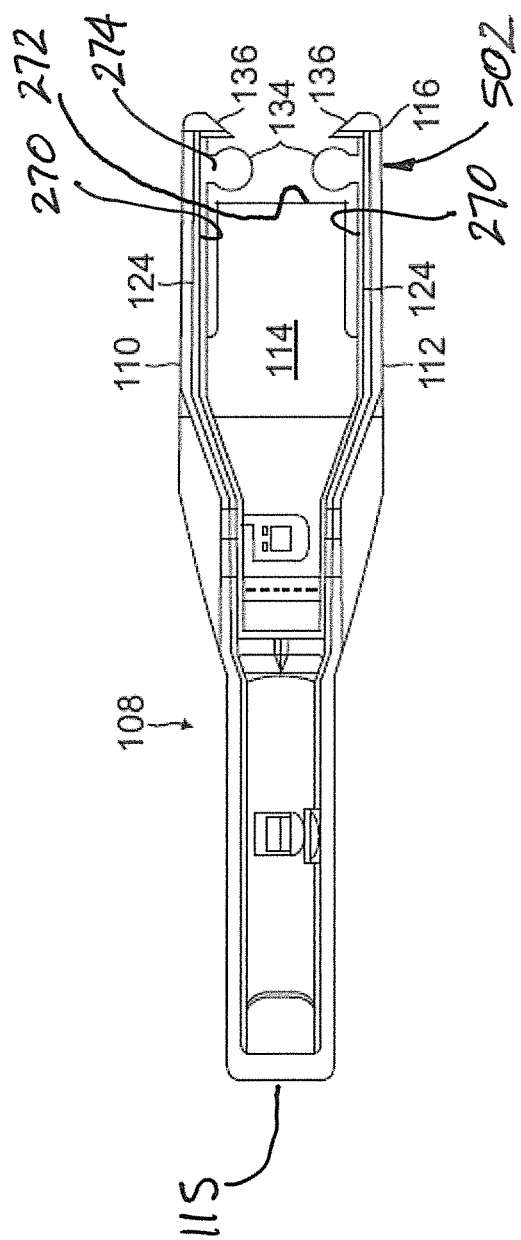
FIG. 2 is a plan view of a shield.
Figure 3:
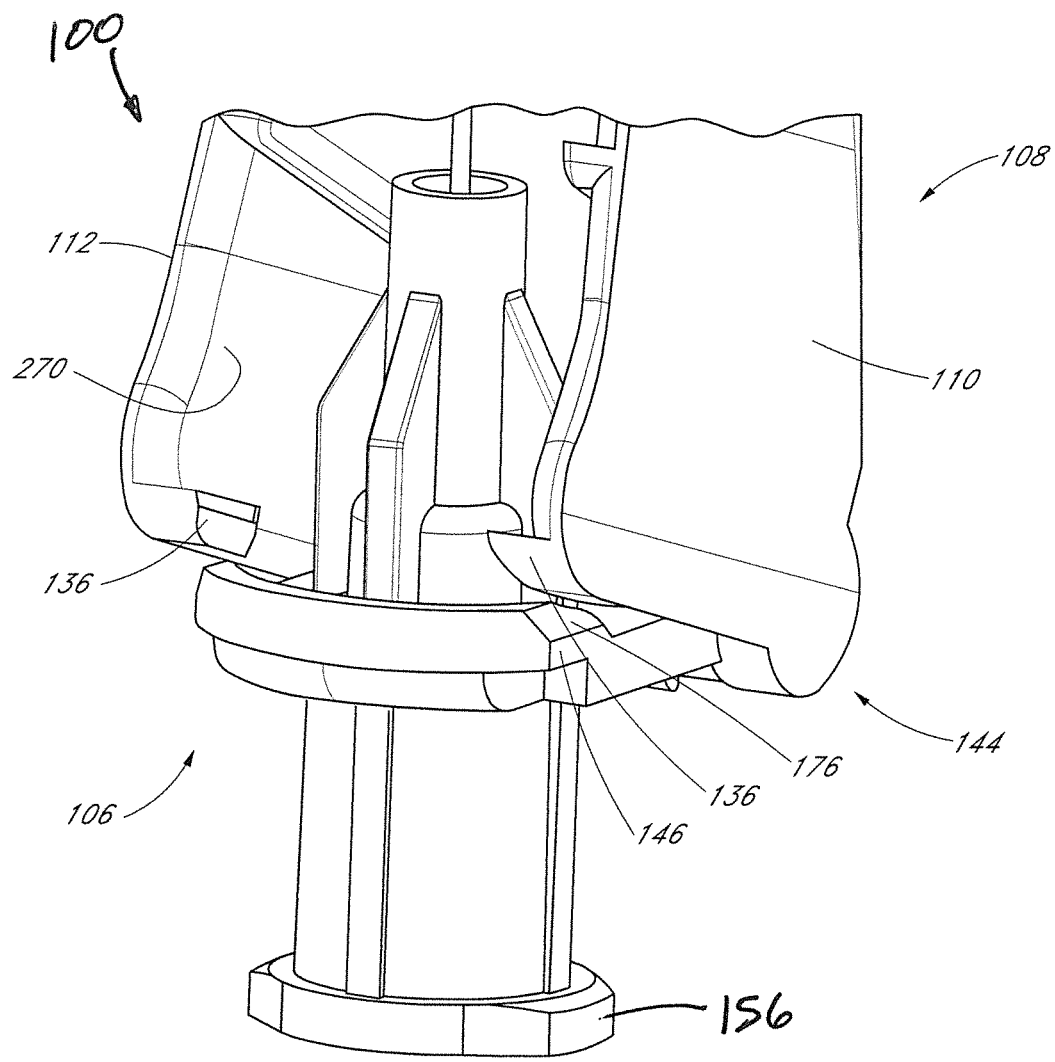
FIG. 3 is a partial side perspective view of another embodiment of the present hinged needle assemblies.

FIGS. 1-9 illustrate different variations or embodiments of hinged shield assemblies and their components in accordance with aspects of the invention. The hinged shield assemblies described herein may alternatively be referred to as hinged needle assemblies, hinged cap assemblies, or hinged cap devices. As shown in FIG. 1, the hinged shield assembly 100 comprises a shield 108 for shielding a needle 104 extending from a needle hub 106. In the example shown, the needle 104 is secured to a central post or cylinder post 280 formed with the needle hub 106. In another example, the needle hub 106 does not include a needle but comprises a male Luer where the central post 280 is located for receiving a separately formed female Luer hub having a needle attached to the separately formed needle hub. The needle hub 106 shown in FIG. 1 has a female Luer with external threads 156 (FIG. 3) for receiving a male Luer, optionally with a threaded collar. With reference to FIGS. 1 and 3, the shield 108 is pivotable about the hub 106 to expose the needle 104 for performing a medical procedure and to cover the needle 104 following use. As described in further detail below, the shield 108 is configured to be manipulated from a packaged position (FIG. 1, similar to when the device is packaged in a plastic overwrap) to a ready-to-use position in which the needle is exposed, from the ready-to-use position to an open position in which the shield is rotated clear of the needle for use, and from the open position to a secured position or protected position in which the shield 108 is rotated to cover the needle 104 and locks to the needle and/or to the needle hub 106 to prevent or deter re-exposing the needle after it has been used.

FIG. 1 shows the assembly 100 in a packaged position, which typically includes a conventional blister pack for packaging the assembly therein. When the assembly 100 is manufactured and packaged, it includes a removable cap 188 for capping the sharp distal tip or needle tip 186 (FIG. 1) of the needle 104 prior to use and for packaging. The tapered removable cylindrical cap 188 fits over the distal cylindrical portion 154 of the needle hub 106 in a friction fit. The cap 188 is sufficiently long to accommodate the length of the needle 104 and can be long enough so as to fit over several different sized, such as different lengths, needles. An outer diameter of the cap 188 is sized so that the width of the shield 108 can only extend around part of the removable cap 188, enabling the base end 116 of the rear wall 114 of the shield 108 to be spaced from the cap 188 and the shield 108 capable of pivoting towards the cap 188 as shown in FIG. 1, in which the shield 108 partly covers the cap 188. Each sidewall has a base end 116. In this configuration, the assembly 100 occupies a relatively smaller profile, such as a relatively smaller space, for shipping as compared to a configuration in which the shield 108 extends perpendicularly to the cap 188 or not overlap with any part of the removable cap 188. The removable cap 188, the needle hub 106, and the shield 108 may be made from conventional materials.

Figure 8:
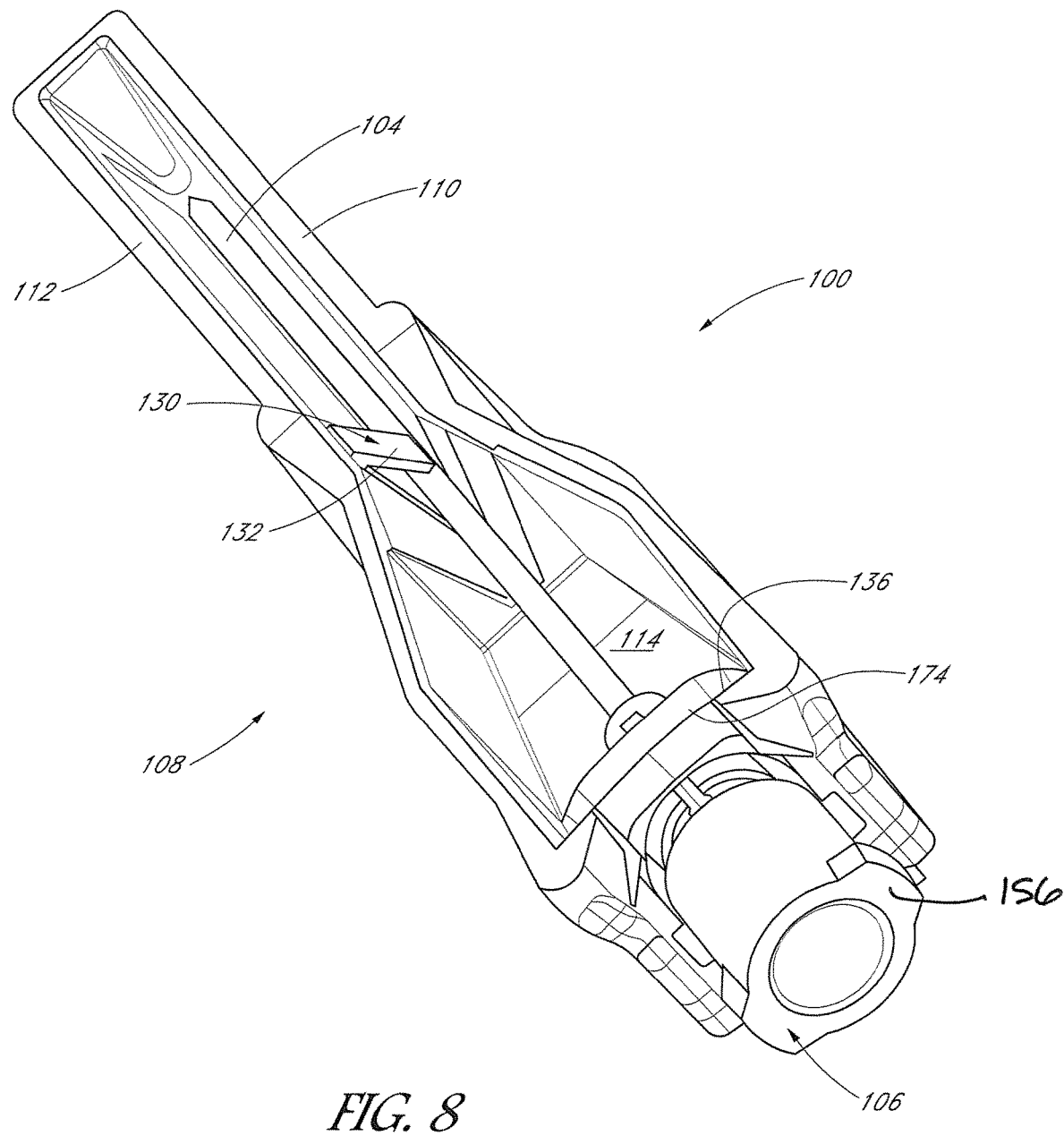
FIG. 8 is a perspective view of another embodiment of the present hinged needle assemblies.
Figure 9:
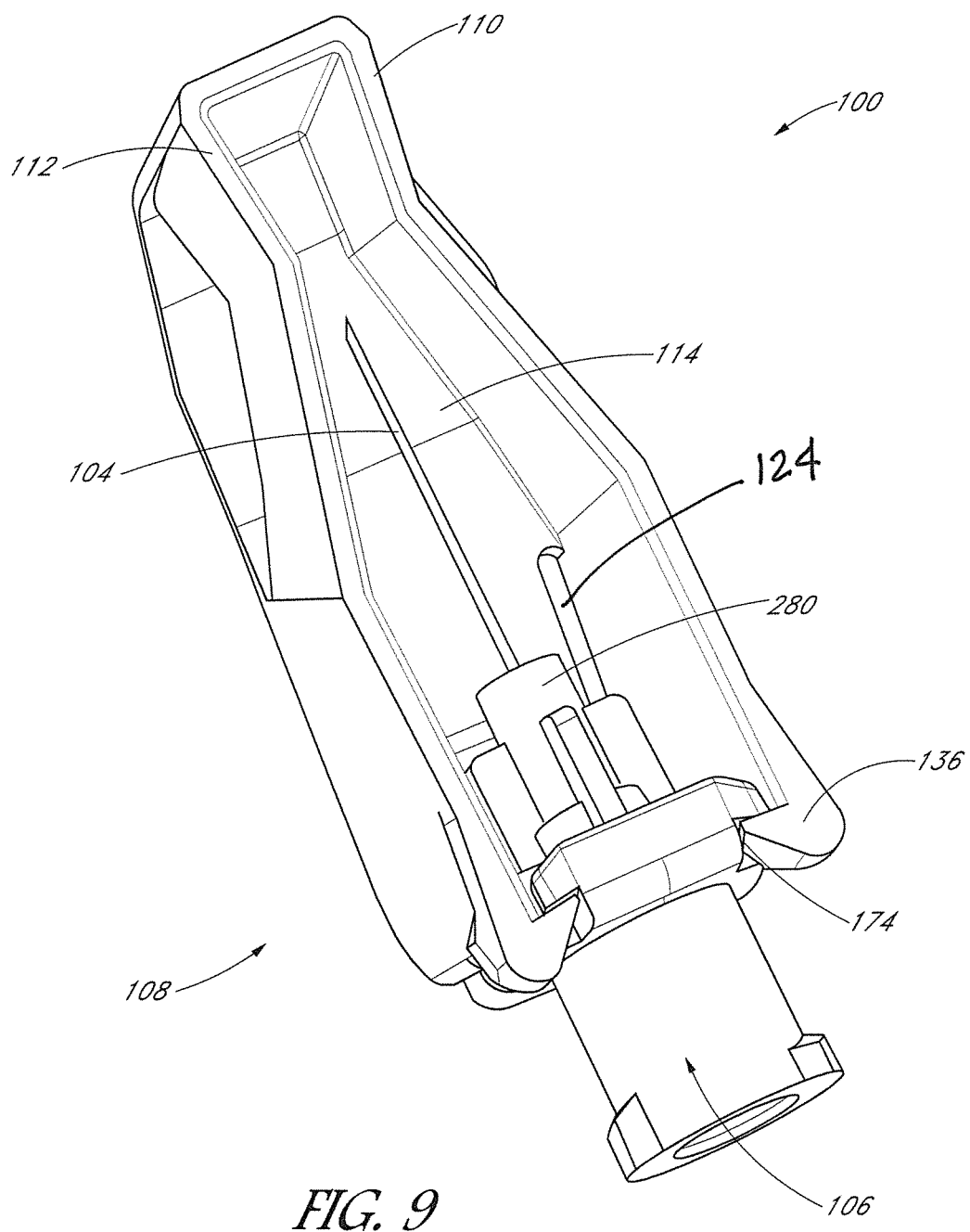
FIG. 9 is a perspective view of yet another embodiment of the present hinged needle assemblies.

With reference to FIGS. 2, 8 and 9 in addition to FIG. 1, the shield 108 comprises a plurality of sidewalls, including first, second and third sidewalls 110, 112, 114 defining an interior space configured to surround the needle 104 on at least three sides. The third sidewall 114 may also be referred to as a center wall, central wall, or rear wall and is positioned between the first and second sidewalls 110, 112. With reference to FIGS. 1, 4, 8 and 9, the first and second sidewalls 110, 112 are generally parallel to one another at a base end 116 of the shield 108, then taper toward one another, and then continue parallel to one another. Other sidewall contours are contemplated, such as having two sidewalls 110, 112 that extend generally parallel to one another along their entire lengths or slightly taper along their entire lengths or along only part of the lengths. With reference to FIG. 1, the third sidewall 114 is contoured from a sloping base portion 118 to a bulging portion 120. The third sidewall 114 may also be generally flat or can be undulating. An outside surface of the bulging portion 120 can include transverse ridges 122 to facilitate gripping the shield 108, such as to be pushed by a finger to close the shield 108 over the needle 104. As shown in FIG. 2, all three sidewalls 110, 112, 114 are joined at approximately 90° angles. In some examples, the first and second sidewalls 110, 112 can diverge or converge along the direction away from the third sidewall 114 and therefore not formed at 90° angles. Near the base 116 of the shield 108, the first and second sidewalls 110, 112 are slightly spaced from the third sidewall 114, forming first and second slits 124. The slits 124 enable the first and second sidewalls 110, 112 to be bent away, such as to deflect, from one another or relative to one another so that the spacing between the two sidewalls 110, 112 at the base can vary due to the deflection, such as be closer or further away from one another compared to when they are not deflected, to facilitate mounting the shield 108 on the hub 106 (FIG. 1) during manufacture, as further described below. As shown in FIG. 3, the end of the shield 108 near the base end 116 is wider than the end of the shield 108 near the end wall 115, formed by a reducer or enlarger somewhere in between the two ends 115, 116. In other examples, the width of the shield 108 is about the same at both ends 115, 116.

With reference again to FIG. 1, the sidewalls 110, 112, 114 extend approximately half the length of the shield 108 and adjoin a shoulder portion 126 that extends transversely inward from the edges of all three sidewalls 110, 112, 114. A shroud 128 extends from the shoulder portion 126 away from the sidewalls 110, 112, 114. The shroud 128 has a substantially U-shaped cross-section. The shroud 128 is closed at its end opposite the base end 116 of the shield 108. The shield 108 is open along one side to accommodate passage of the needle 104 as the shield 108 pivots with respect to the hub 106, as explained in detail below. The shield 108 may also be viewed as having three sidewalls 110, 112, 114, that extend the entire length of the shield with the central wall 114 having the shoulder 126. The so-called shroud 128 is subsumed within the three sidewalls 110, 112, 114. The end wall 115 at the end opposite the base 116 is connected to all three sidewalls and formed a closed top end 125.

With reference again to FIG. 2, the base end 116 of the shield 108 includes first and second ball hinge components or balls 134 and first and second tabs 136. The balls 134 extend inwardly from inner surfaces 270 of the first and second sidewalls 110, 112. In an example, the balls 134 and the tabs 136 are located on the first and second sidewalls 110, 112 at locations further away from the end wall 115 than the end edge 272 of the central wall 114. The tabs 136 can also extend inwardly from the inner surfaces 270 of the first and second sidewalls 110, 112. In an example, the tabs 136 extend from corners of the two sidewalls 110, 112 at the base end 116 opposite those from which the balls 134 extend. In some examples, the tabs 136 can be formed on the inner surfaces 270 of the first and second sidewalls at locations other than the corners, such as inwardly or recessed from the corners to engage different points on the needle hub 106. In an example, the balls 134 are spherical and each includes a projection or stub 274 connecting the ball to the respective sidewall. The length of each projection 274, if more than one ball 134 are included, can be adjusted to control the depth that the ball attached thereto projects into a corresponding socket, as further discussed below. In other examples, the balls 134 are elongated, similar to tear drops or water drops. Each ball may optionally include surface features, such as ridges, fins, dimples, or projections, which can alter surface contacts between the balls and the sockets to which they connect, as further discussed below.

Figure 4:
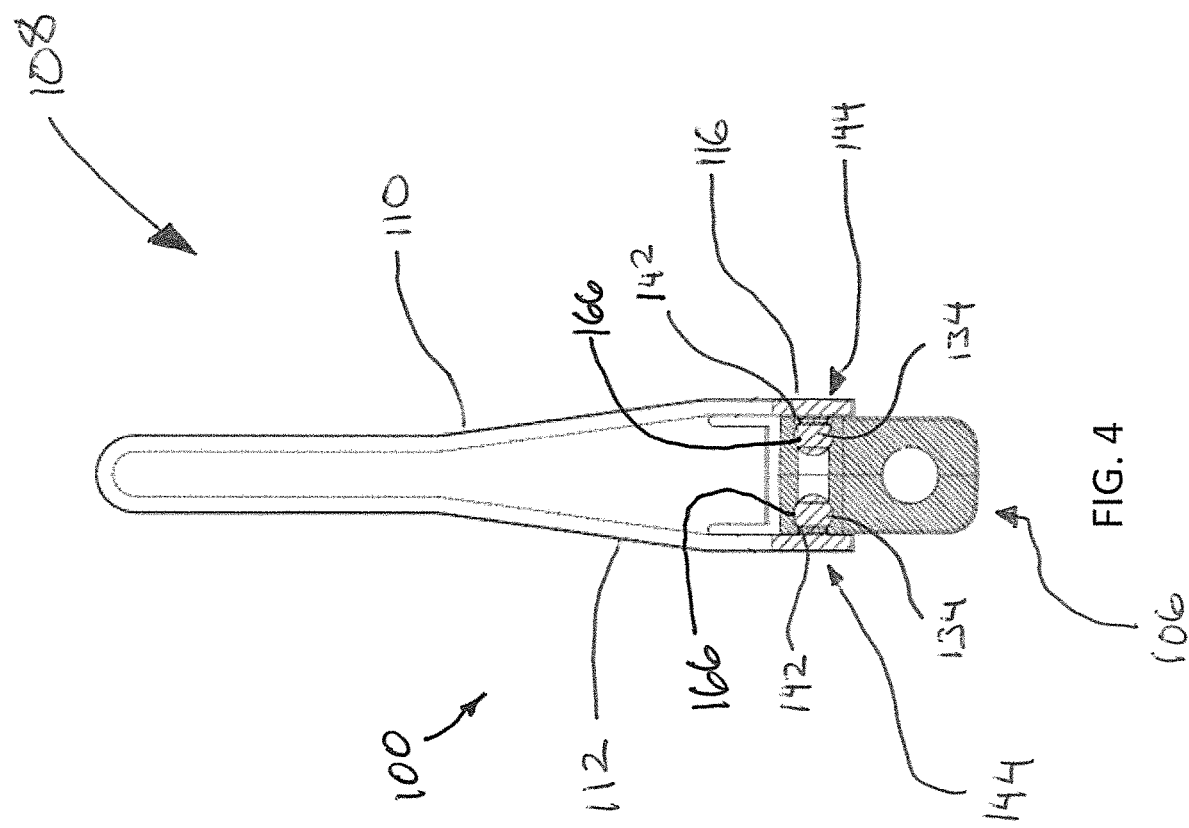
FIG. 4 is an top view of the hinged shield assembly of FIG. 3.
Figure 5:
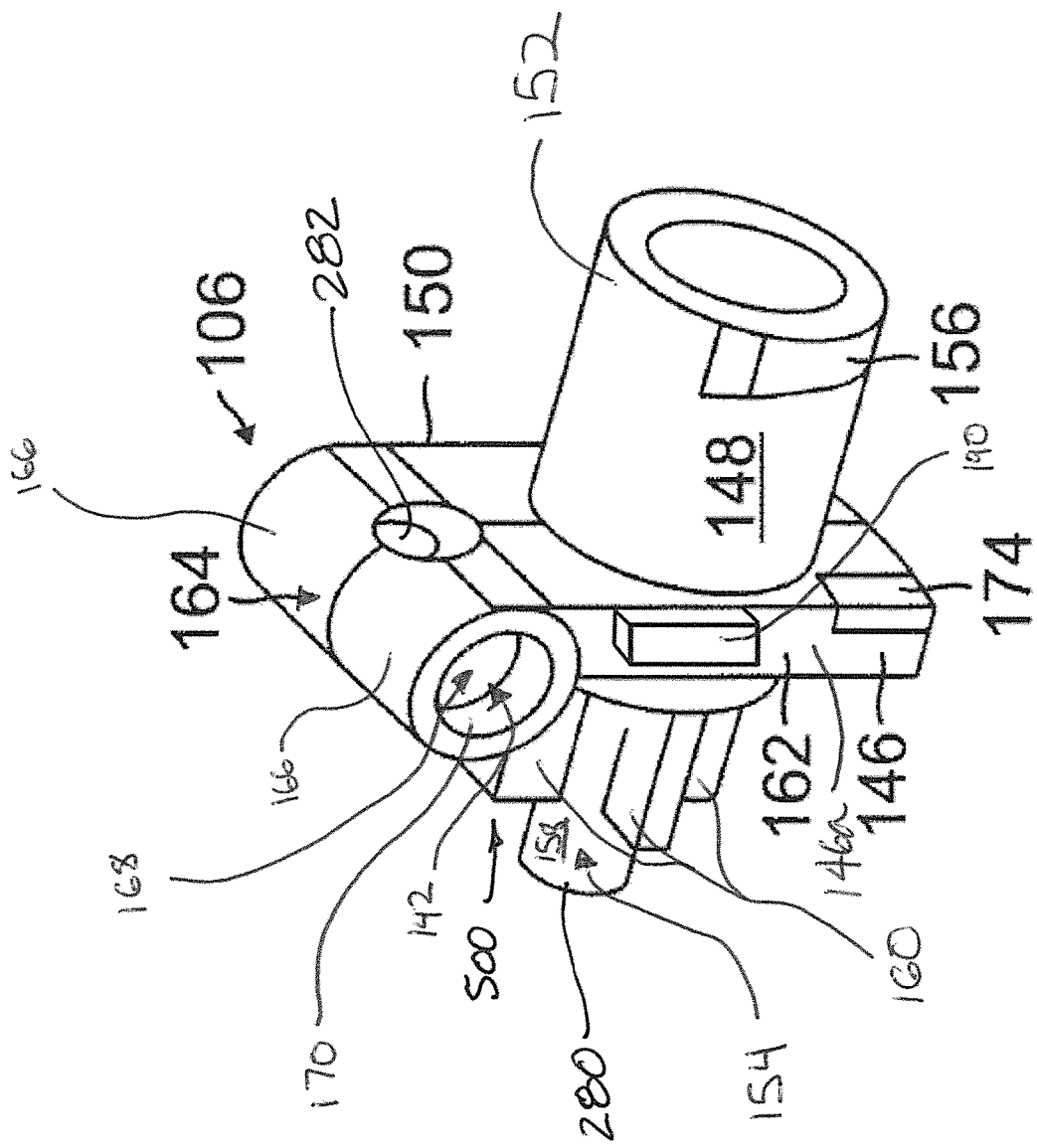
FIG. 5 is a perspective view of an embodiment of a hub in accordance with the present hinged needle assemblies.

With reference to FIGS. 3, 4 and 5, the balls 134 are configured to be received within sockets 142 located on the hinge component 164 of the needle hub 106 to form a ball-and-socket hinge 144 for pivotal movement of the shield 108 and hub 106 with respect to one another. Thus, the present disclosure is understood to include a first hinge component formed with the shield 108 for attaching to a second hinge component formed with the needle hub 106. In one example, the two sockets 142 share a common bore. In another example, the two sockets 142 are isolated from one another, such as by a wall, a gap, or a channel such that the hinge component 164 can be thought of as comprising two separate components for receiving the two balls 134. For instance, two cups or sockets 142 may be provided to receive two balls 134. The two cups can each include a round bore and a curved end wall to close the bore. The two curved end walls of the two cups can be spaced from one another. Thus, the hinge 144 can be understood to include two or more separately formed components, i.e., a multi-piece structure, that are joined together to form a movable hinge. The hinge 144 is understood to include a first hinge component attached to a second hinge component. The hinge can comprise a ball-and-socket joint 166. As shown, two ball-and-socket joints 166 are provided to form the hinge 144 of the present disclosure. The hinge 144 can be characterized as a ball-and-socket hinge comprising two ball-and-socket joints 166, which include two balls 134 and two sockets 142. More generally speaking, the needle hub is understood to include a first hinge part or component 500 and the shield includes a second hinge part or component 502 that engages the first hinge part to pivotably secure the shield 108 to the needle hub 106. The first hinge part can be understood to comprise a hinge component having sockets, which may have a common bore or be spaced from one another by a gap or a wall. The second hinge part can be understood to comprise balls, such as two spaced apart balls.

Figure 6:
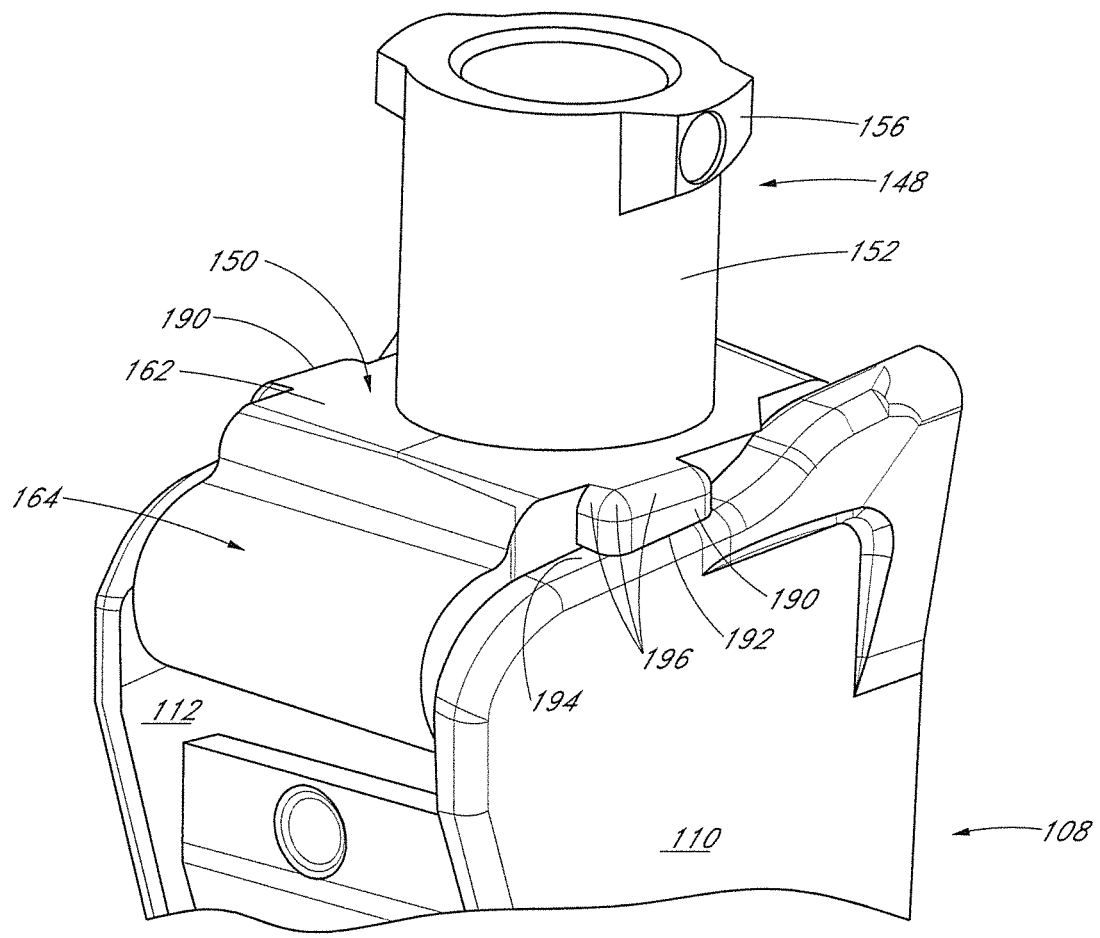
FIG. 6 is a perspective view of another embodiment of a hub of the present hinged needle assemblies.

When the assembly 100 is manufactured, the shield 108 is assembled to the hub 106 by flexing the first and second sidewalls 110, 112 (FIGS. 2 and 3) away from each other in the area of the base end 116 of the shield 108. The slits 124 (FIG. 2) between the first and second sidewalls 110, 112 and the third sidewall 114 facilitate the flexing. The shield 108 and the needle hub 106 are then positioned such that the balls 134 are just outside the openings 168 (FIG. 5) of the two sockets 142. The sidewalls 110, 112 are then forced inward so that the balls 134 squeeze through the openings 168 and into the sockets 142. The perimeters defining two openings 168 are smaller than the maximum outside diameters of the two balls so that the balls and/or the perimeters defining the openings deform during the engagement. In one example, the two perimeters have the same opening diameter and the two balls have the same outside diameters. In other examples, the diameters of the perimeters are different from one another and the diameters of the two balls are different from one another. One or more openings 282 may be provided with the base at the sockets 142 for relief but can be omitted, as shown in FIG. 6. As shown in FIG. 3, as these steps are performed, the shield 108 is positioned at an appropriate angle relative to the hub 106 so that the tabs 136 and/or sidewalls 110, 112 do not interfere with the hub 106 during the assembly. For example, the shield 108 and hub 106 may be positioned such that their longitudinal axes are perpendicular to one another, as shown in FIG. 4, during assembly.

To use the present hinged shield assembly 100, an operator typically begins with the assembly 100 in the packaged configuration of FIG. 1, such as by first removing the overwrap. The operator then pivots the shield 108 away from the cap 188 and removes the cap 188 to expose the needle 104. The assembly 100 is then ready to be used to inject medication or to draw blood. Advantageously, the ball-and-socket hinge 144 enables the shield 108 to be retained at any desired angle with respect to the needle 104 without the need for the operator to hold the shield 108 on one hand while using the assembly with the other hand. For example, because of the interference fit between the balls 134 and the sockets 142, the tight fitting arrangement allows the interior surfaces of the sockets 142 to grip the balls 134 at any number of angles of the shield relative to the needle hub 106. Thus in use, the operator's fingers are available to perform other tasks without having to hold the shield 108 in the open position or in any particular position while attempting to use the assembly 100. The relative sizes and/or shapes of the balls 134 and the sockets 142 can be tailored to provide desired relative motion and interference, or even non-interference, which is less preferred. For example, these components can be manufactured for an interference fit so that friction and interference between the moving parts retains the shield 108 at the desired angle after the operator releases the shield 108.

The diameter of the sockets 142 that receive the balls 134, as shown in FIG. 4, may be changed in a number of ways. Each ball 134 has a diameter that is approximately equal to the maximum diameter of each socket 142, but greater than the diameter of the opening 168 (FIG. 5). Thus, in assembling the balls to the sockets, the balls and/or the perimeters defining the openings of the sockets deform in order for the assembly to occur. The balls can be sized to also be larger than the sockets to form an interference fit. The balls 134 thus sit within the sockets 142 and resist withdrawal from the sockets 142 because the opening 168 has a smaller diameter than the largest diameter of each ball 134. The openings to the sockets have a diameter that is smaller than the internal diameters of the sockets. In other words, right at the opening 168, the opening diameter has a first dimension and inside the opening 168 at the socket, the bore diameter of the socket has a second dimension, which is larger than the first dimension at the opening. The relative sizes of the balls 134 and sockets 142 can be tailored to provide a desired amount of resistance to rotation of the balls 134 within the sockets 142 and degree of interference. Also, the shapes of the balls 134 can be tailored to provide a desired smoothness of motion, or lack of smoothness, as described below.

In alternative embodiments, alternative shapes for the outer surfaces of the balls are provided. Possible alternative shapes include various regular and irregular polyhedrons having a plurality of faces. Examples of regular polyhedrons include dodecahedron, icosahedron, octahedron, or any other polyhedron. Each of these shapes includes a plurality of faces having congruent shapes. In an irregular polyhedron the faces do not have congruent shapes, and the faces may extend partially or fully around the circumference of the ball. These alternative shapes provide a plurality of faces that form planes extending perpendicularly to the first and second sidewalls 110, 112. The faces may extend partially or fully around the circumference of the ball 134. Corresponding faces may be provided in the socket 142 so that as the shield 108 pivots the faces on the ball 134 sequentially abut the faces in the socket. The resulting motion provides a ratchet-like effect, which can be thought of as tactile feedback, which enables the shield 108 to be held at a variety of different angles with respect to the needle 104 and provide feedback as the shield rotates. In other examples, the balls 134 have dimples, similar to a golf ball.

With reference to FIG. 8 in addition to FIG. 1, the shield 108 further comprises at least one hook 130 that extends inwardly from the third sidewall or rear wall 114 and/or from the shroud 128, such as from the center wall of the shroud. But when the entire shield 108 is simply identified as having three sidewalls extending the entire length of the shield as previously described, the at least one hook 130 extends from the third sidewall from any number of points along the length of the third sidewall towards the open space defined by the gap between the first and second sidewalls 110, 112. In some examples, one or more hooks 130 can extend from one of the two sidewalls 110, 112 rather than the rear wall. In the embodiment illustrated in FIG. 1, the two hooks 130 are formed integrally with the shield 108, such as being singularly molded with the third sidewall 114. The hooks 130 are configured to capture the needle 104 after use when the shield 108 is pivoted toward the needle 104 to secure the shield 108 in the needle-protected position or simply protected position, which is discussed in more detail below. In addition to the one or more hooks, tabs 136 may be used to removably secure the shield 108 to the needle hub 106 to provide stability. The shield 108 may also be formed without hooks as shown in FIG. 9. For example, when used with a small diameter needle gauge, the hooks may be omitted and the securement may be between the shield 108 and the needle hub 106. In embodiments without any hook 130, more permanent secure means may be incorporate to prevent separation between the shield 108 and the needle hub 106 after their engagement and following use of the needle.

The hooks 130 automatically catch the needle 104 upon closing the shield 108 over the needle 104. As the shield 108 pivots toward the needle 104, a ramped or rounded end surface 132 of each hook 130 contacts the needle 104, flexing the hook 130 laterally to allow the hook 130 to snap around and capture the needle 104. In other examples, one hook or more than one hook may be incorporated, such as that shown in FIG. 1 with two hooks. In still other examples, the location of the hooks may be changed so that the hooks secure different sections of the needle and/or the needle hub. For example, one hook can snap and lock against the central post 280 holding the needle while a different hook can lock against the needle. In still other examples, one hook is used to secure against the central post while tabs are used to secure against the transverse wall base on the needle hub 106.

With reference again to FIG. 3, tabs 136 are formed on the interior of the sidewalls 110, 112 and configured to be received beneath ledges 146 comprising side edges on the needle hub 106 to secure the shield 108 to the needle hub 106 in the needle-protected position. These aspects are described in detail below. On the corners opposite the sockets 142 (FIG. 5), the hub 106 includes side edges 146a having notches 174 on the side of the transverse base 150 opposite the sockets 142. The transverse base 150 and the notches 174 are formed as recesses on the planar surface 162 (FIG. 5). The notches 174 are sized and shaped to be complementary to the tabs 136 on the shield 108. The tabs 136 snap into the notches 174 when the shield 108 is pivoted toward the protected position to hold the shield 108 in that position. For example, any attempt to open the shield 108 will be resisted by the tabs 136 abutting against the notches 174. However, the engagement is separable as a user can simply pride the tabs 136 from the notches 174 to separate their engagement. When closing the shield 108 over the needle 104, the two sidewalls 110, 112 deflect and the deflection is aided by the slits 124 formed on the shield 108 when the tabs 136 snap into the notches 174. With reference to FIG. 3, the surfaces 176 of the ledges 146 on the transverse base 150 on the side opposite the notches 174 are ramped or tapered so that as the shield 108 pivots toward the protected position, the tabs 136 slide over the ramp surfaces 176 and deflect outwardly, such as by camming action, and the two sidewalls 110, 112 expand outwardly as they slide thereover. When the tabs 136 slide around the ledges 146, the two sidewalls 110, 112 recoil to snap the two tabs 136 into the notches 174 to secure the shield 108 to the needle hub 106 in a protected position. This securement by the tabs 136 against the notches 174 stabilizes the shield 108 when an attempt is made to push the shield 108 back open, which is stronger and more stable compared to the shield 108 only hooking onto the needle 104. However, the locking action provided by the tabs 136, the notches 174 and the ledges 146 is reversible. An operator may apply digital pressure to flex the first and second sidewalls 110, 112 away from one another. By flexing the sidewalls sufficiently, the tabs 136 can clear the notches 174 and the ledges 146 so that the shield 108 can be pivoted away from the protected position. Conversely, the hook or hooks 130 extending from the third sidewall 114 form locking mechanisms that are more difficult if not impossible to reverse when they hook around the needle 104 and/or the central post 280 on the needle hub 106. Due to the confined space inherent in the design, these hooks 130 provide little access to enable un-hooking once they engage and therefore serve to lock the shield to the needle hub.

Figure 7:
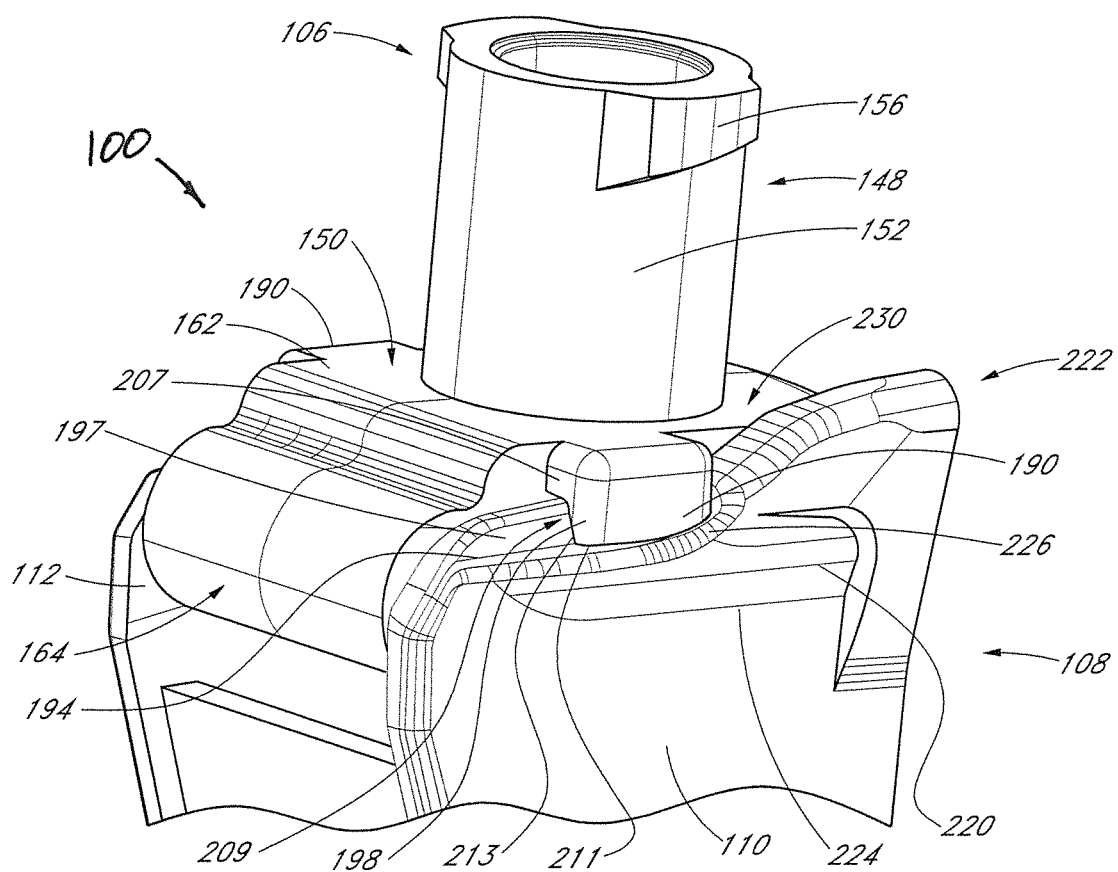
FIG. 7 is a perspective view of yet another embodiment of a hub of the present hinged needle assemblies.

FIGS. 5-7 illustrate an exemplary needle hub 106 in detail in accordance with aspects of the present invention. The exemplary needle hub 106 includes an elongated portion 148 and a transverse base portion 150. The transverse base portion 150 substantially bisects the elongated portion 148, defining a proximal elongated portion 152 and a distal elongated portion 154 (FIG. 13). As shown, both the proximal and distal elongated portions are generally cylindrical. The proximal cylindrical portion 152 is shaped as a smooth hollow cylinder with a female Luer and includes external threads 156 at its proximal end. The threads 156 is configured to engage a female thread at a distal end of a syringe (not shown) to secure the hinged cap device 100 to a male tip, such as a Luer tip of a syringe. The distal cylindrical portion 154 includes a hollow cylinder 158 defining the central post 180 for holding a needle 104. The hollow cylinder 158 optionally comprises one or more fins 160 extending outwardly and parallel to an axis of the cylinder 158. When incorporated, the one or more fins 160 can also be used as retention features for the removable cap 188 (FIG. 1) to engage, such as to frictionally grip. Four evenly spaced fins 160 are shown, but any number may be provided, including less than four or greater than four. The hollow cylinder 158 is configured to receive the blunt proximal end of a needle 104 in a glued engagement with the needle 104 disposed inside the cylinder 158, as shown in FIG. 1. In an alternative embodiment, the engagement with the needle can be a press-fit engagement.

The transverse base portion 150 includes a substantially planar portion or flange 162 bisecting the two cylindrical portions 148, 154, at least along external surfaces, and has, at one end or one edge, a hinge component 164, which in the present embodiment is a substantially cylindrical portion 164. The cylindrical portion 164 on the flange 162 may optionally incorporate a projection or a physical barrier on an exterior thereof to serve as a shield stop to limit how far the shield can rotate away from the needle 104 in an open position. For example, the projection on the cylindrical portion 164 may act as a spacer to restrict the amount of rotation of the shield 108 from the position over the needle to a position rotated away from the needle. In an example, the cylindrical portion 164 comprises first and second socket parts or joints 166 of the ball-and-socket hinge 144. Each socket part 166 may also be referred to as a cup-like depression, such as a socket, for receiving a correspondingly shaped ball. Each socket part 166 includes a perimeter defining an opening 168 having a beveled rim 170. From the opening 168, the diameter of the socket part 166 varies from a relatively narrow opening 168, with the diameter increasing inward of the opening 168 and then gently tapering down to a more narrow diameter. This variable diameter opening is configured to receive a ball of the ball and socket hinge. Of course, the socket 142 can have a variable interior surface contour to create varying interference with the ball when the ball is received therein. Generally speaking, a socket 142 that forms fit with a ball 134 in a ball-and-socket joint is useable as a hinge in a hinge cap device of the present disclosure and wherein an interference between the hinge components is also applicable as a ball and socket joint of the present disclosure. The interference fit is appropriate to enable the shield to be self-supporting at any number of open position or angular position and remain in that position when rotated without freely swinging or rotating due to gravity and without requiring external support. This allows a user to operate the assembly 100 without having to hold the shield 108 when obtaining a sample or when performing an injection. Ball-and-socket joints are a special class of joints that enjoy the highest freedom of motion thanks to their unique structure. For example, a ball-and-socket joint can be rotated along multiple axes and have built-in support bearings compared to a simple pin and hole arrangement, such as those typically used with a door hinge, which is limited to a single rotational axis.

As shown in FIG. 5, the substantially planar portion or flange 162 can comprise one or more stop pieces 190. In an example, a single stop piece 190 is incorporated to stop the shield 108 from over rotation when closing the shield 108 over the needle 104 following use, as further discussed below. In other examples, two or more stop pieces 190 are incorporated with the hinged needle assembly 100. For example, two stop pieces 190 may be incorporated on opposite sides of the transverse base 150. In an example, the flange 162 has a side edge 146a comprising a stop piece 190. In the embodiment shown, the flange 162 has two side edges 146a, each with a stop piece 190 for a total of two with additional stop pieces contemplated. The two stop pieces 190 are generally in the form of a parallelepiped base or simply base 207 (FIG. 5), which extends outward, such as radially outward relative to a lengthwise axis of the needle hub, from the substantially planar portion of the two side edges 146a, on a side or sides of the assembly adjacent to the hinge component 164. The stop pieces 190 are placed in the rotational path of the first and second sidewalls 110, 112 of the shield 108 as the shield rotates around the hinge component 164. The parallelepiped base of the stop pieces 190 is formed with squared off edges but tapered or rounded corners are contemplated. The top of parallelepiped base can be even with the top of the substantially planar portion or flange 162, but the parallelepiped base is not as deep or thick as the substantially planar portion. The stop pieces 190 are also not as wide as the substantially planar portion or flange 162. In other words, each stop piece 190 only occupies a section of the side edge of the transverse base 150 and not the entire width of the transverse base, although theoretically a wider stop piece 190 may be incorporated that is about the same width as the transverse base. The top surface of each stop piece 190 can also be offset from the top of the planar portion 162. In some examples, the stop pieces 190 can extend radially outwardly a greater distance than the width of the shield 108 measured between the two exterior surfaces of the sidewalls 110, 112 or can be short of the distance between the two sidewalls. If the stop pieces 190 extend a greater radial distance, they can stop the shield from over-rotation even if the shield spreads or widens, such as distort, upon contacting the stop pieces 190. Once the shield 108 contacts at least one stop piece 190, the base end 116 of each of the sidewalls 110, 112, 114 is prevented from moving past, such as further rotating, beyond an at rest point when the shield 108 is in a protected position in one rotational direction. In the protected position, the shield 108 covers the needle 104 and locks against either the needle 104, the central post or distal cylindrical portion 154, or the needle hub 106, such as the transverse base 150.

In the embodiment of the needle hub 106 shown in FIG. 6, the substantially planar portion 162 incorporates two stop pieces 190, each of which comprising a planar surface to abut the shield 108. The stop pieces 190 each includes a flat distal side 192, which is configured to make contact a proximal edge or contact edge 194 of the shield 108. The stop piece shown in FIG. 6 includes rounded edges 196 on the proximal side of the stop piece 190. The stop pieces 190 may be placed or positioned along the two side edges 146a of the planar portion or flange 162, such as anywhere between the notch 174 and the socket 142 (FIG. 5). The locations of the distal surfaces 192 of the two stop pieces 190 relative to the flange 162 may also vary depending on where the contact edges 194 of the first and second sidewalls 110, 112 contact the stop pieces 190 during closing rotation of the shield 108. The placement of the stop pieces 190 should also be selected in conjunction with the design and placement of the hooks 130, the tabs 136, and the notches 174 so that collectively they allow locking of the shield 108 to the needle hub 106 without interference. In one example, the stop pieces 190 and the first and second sidewalls 110, 112 of the shield 108 can have latching or locking detents so that when the sidewalls 110, 112 abut the stop pieces 190, the latching or locking detents prevent the shield 108 from separating from the hub 106 and re-open to expose the needle 104.

Yet another alternative embodiment of a needle assembly 100 is shown in FIG. 7. The needle assembly 100 has a needle hub 106 and a shield 108 connected to the needle hub in a ball-and-socket arrangement, similar to that shown in FIGS. 1-5. In the present embodiment, the transverse base portion 150 includes two stop pieces 190, on opposite sides of the substantially planar side edges 146a and corresponding to the sides of the two sidewalls 110, 112. The stop pieces 190 in the present embodiment each includes a parallelepiped base, or simply a base, 207, similar to the stop piece of FIG. 6. Each base 207 can be viewed as a radially extending member in that it extends radially of the lengthwise axis of the needle. In addition, the stop pieces 190 of the embodiment of FIG. 7 each includes a longitudinally extending member, capture element, or capture portion 198. The capture elements or portions 198 extend directly from the two respective bases 207. In one example, the base 207 and the capture portion 198 of each stop piece 190 form a generally "L" shape structure when viewing from an end. In other examples, the base and the capture portion can have other shapes, such as a "T" shape. Each capture portion 198 can be viewed as an axially extending member in that it extends along the same axial direction as the lengthwise axis of the needle. The capture portions 198 on the two stop pieces 190 are sized and shaped to overlap a reduced depth portion 197 of the shield sidewall 110, 112. This reduced depth portion 197 of each sidewall extends transversely, beginning near the hinge component 164 and ending near the middle of the each of the first and second sidewalls 110, 112 and has a dimension that is smaller or less than other depth portions, such as being thinner in dimension compared to other wall surfaces of the same sidewall. The base 207 and the capture portion 198 of each stop piece 190 define a gap or retention space 209 for accommodating the reduced depth portion 197 of the respective sidewall. The two capture portions 198 of the two stop pieces restrict the first and second sidewalls 110, 112 from deflecting radially outwardly away from the lengthwise axis of the needle hub to slip past the two stop pieces and over-rotate. In some examples, only a single stop piece 190 having a base 207 and a capture portion 198 is incorporated with the transverse base portion 150.

The present stop pieces 190 are understood to not only stop the shield 108 from over-rotation by providing radially extending stop surfaces to interfere with the two sidewalls 110, 112 as they rotate, they also prevent or limit outward radial deflection of the two sidewalls 110, 112 by capturing the two sidewalls within retention spaces 209 defined at least in part by the two capture portions 198. In one example, each stop piece comprises a radially extending member and an axially extending member. For example, the base 207 can form a radially extending member and the capture portion 198 can form an axially extending member, both relative to a lengthwise axis of the needle hub or the needle. Thus, aspects of the present disclosure are understood to include at least one of the plurality of sidewalls of the shield 108 contacting the at least one stop piece to prevent over rotation of the shield 108 in one rotational direction when the shield 108 is in a protected position over the needle 104. Another aspect of the present disclosure is understood to include means for limiting outward radial deflection of at least one of the plurality of sidewalls of the shield. The means can include a capture portion 198 extending from a base 207 on a stop piece 190. In other examples, the bases 207 of the stop pieces 190 extend sufficiently radially so that the corresponding sidewalls on the shield can be received within the retention spaces 209 without the need for incorporating reduced depth portions 197 on the sidewalls. In some examples, the edge of each sidewall can also be enlarged and the retention spaces 209 are sized and shaped to accommodate the enlarged sections of the sidewalls.

As described above, as a user rotates the shield 108 to a closed position over the needle 104, the tabs 136 (FIG. 3) on the shield 108 come into contact with the substantially planar portion 162 of the hub 106. As the tabs 136 come into contact with the substantially planar portion 162, the width of the tabs 136 relative to the width of the planar portion 162 causes the sidewalls 110, 112 on the shield to deflect transversely outwardly, away from the lengthwise axis of the needle and radially of the lengthwise axis of the needle hub 106. This radial deflection of the two sidewalls is greatest at the tabs and decreases as it moves towards the end of the first and second sidewalls 110, 112 with the third sidewall 114. The reduced depth portion 197 of each of the first and second sidewalls slides pass the distal most end 211 of the capture portion 198, between an inside edge 213 of the capture portion 198 and the corresponding side edge 146a of the planar portion 162 transversely opposite the inside edge 213. The process of passing the reduced depth portion 197 between the distal most end 211 of the capture portion 198 between the inside edge 213 of the capture portion 198 and a side of the substantially planar portion 162 effectively captures the respective sidewall 110 or 112 in the retention space 209. Said another way, the capture portion 198 captures the reduced depth portion 197 within the retention space 209 as the shield 108 rotates to close over the needle. In an example, the radially extending portion of each stop piece 190 is sufficiently long or is sized and shaped so that a gap or clearance is provided to ensure sufficient space for the reduced depth portion 197 of the respective sidewall to slide within the retention space 209. In other words, there should be sufficient clearance or tolerance within the retention space 209 to accommodate the respective sidewall of the shield as the sidewall slides inside the retention space.

The contact edge 194 of each sidewall adjacent the reduced depth portion 197 and the distal face 211 of the capture portion 198 of the stop piece can be configured to contact the shield in the shield 108 lock position by providing an increased depth section 220. The increased depth section 220 increases the thickness of each respective sidewall, making the sidewall thicker at and near the base section 222 of the sidewall. The increased depth section 220 starts at a transverse line 224 distal of the proximal edge 194 of the sidewall and transitions from this point away from the sidewall, increasing the thickness such that a rounded proximal edge 226 extends outside of the stop piece 190.

At an end point of the contact edge 194 closest to the hinge component 164, the contact edge 194 is generally parallel to the proximal surface 230 of the substantially planar portion 162. At a halfway point along the contact edge 194, the contact edge surface is still generally parallel to the proximal surface 230 of the substantially planar portion 162. Just past the halfway point in the direction away from the hinge component 164, the contact edge 194 begins to curve, and follows a geometrically proximally curving path. Said another way, as the path of the contact edge 194 moves away from the hinge component 164 and towards the tab 136, the contact edge 194 curves increasingly proximally. In the embodiment shown, the distal face 211 of the capture portion 198 of the stop piece is curved to match the curve of the contact edge 194 along the distal face 211 of the capture portion 198. In other embodiments, the contact edge 194 remains generally parallel to the proximal surface 230 of the substantially planar portion 164 for its entire length, with an angled transition at the opposite end. In these embodiments, the distal face 211 of the capture portion 198 is sized and shaped to match the contact edge, similar to the stop piece 190 embodiment of FIGS. 5 and 6. In some examples, the entire lower portions of the first and second sidewalls are sufficiently narrow or thin to ensure passing into the retention spaces without the contoured surfaces or with less contoured surfaces described.

As shown in FIGS. 8 and 9, the shield 108 pivots to cover the needle 104 when a force is applied to the shield, such as by using digital pressure or pushing the shield against a surface to rotate the shield to a closed position. The shield 108 pivots until the hooks 130 snap around the needle 104 and/or the tabs 136 snap into the notches 174 on the needle hub 106. With the needle 104 safely surrounded by the shield 108, the assembly 100 is ready to be discarded. Note that the needle hinged cap embodiment of FIG. 8 incorporates a single hook 130 to hook around the needle 104 and the needle hinge cap assembly of FIG. 9 does not incorporate any hook extending from the central wall. Instead, the shield 108 FIG. 9 is secured to the needle hub 106 by engaging the tabs 136 on the shield with the notches 174 on the needle hub 106. Optionally, a hook 130 may be provided to hook onto the needle 104 and/or to hook onto the central post 280 of the needle hub 106. The stop pieces and the first and second sidewalls can also incorporate locking detents, as previously discussed, to secure the shield to the needle hub.

As further shown in FIGS. 8 and 9, when the shield 108 reaches the closed position or protected position, the shield 108 is prevented from rotating in the opposite direction, or open direction to re-expose the needle, by the engagement of the tabs 136 with the notches 174 and/or by the hook hooking onto the needle or the post. As shown in FIGS. 6 and 7, in the same closed position or in the process of closing the shield over the needle, the shield 108 is prevented from over rotating by the contact between the stop pieces 190 and the contact edges 194 of the shield 108. When incorporated, one or more stop pieces can be used to prevent the shield from over-rotating. By preventing rotation in either direction when the shield 108 is in the locked position or protected position shown in FIGS. 6 and 7 and elsewhere, the hinged shield assemblies 100 of the present disclosure prevent or deter accidental or intentional reopening of the shield 108.

Methods of making or manufacturing and of using the hinge cap devices discussed elsewhere herein are within the scope of the present disclosure.

The above description presents the best mode contemplated for carrying out the present hinged shield or hinged cap assemblies, and of the manner and process of making and using them, in such full, clear, concise, and exact terms as to enable any person skilled in the art to which they pertains to make and use these hinged shield assemblies. These hinged shield assemblies are, however, susceptible to modifications and alternate constructions from that discussed above that are fully equivalent. Consequently, these hinged shield assemblies are not limited to the particular embodiments disclosed. On the contrary, these hinged shield assemblies cover all modifications and alternate constructions coming within the spirit and scope of the hinged shield assemblies as generally expressed by the following claims, which particularly point out and distinctly claim the subject matter of the hinged shield assemblies.

The invention claimed is:

1. A hinged shield assembly comprising:
   a needle hub comprising a cylindrical portion having an exterior surface and a hollow interior sized and shaped to receive male tip of a syringe, a first socket having a bore, and a second socket having a bore, the two bores of the first and second sockets align with one another;
   a needle having a needle shaft with a needle tip and a lengthwise axis;
   a shield comprising sidewalls that partially surround the needle when the shield is in a protected position, said shield further comprising a hook extending between the sidewalls for engaging the needle or a tab for engaging the needle hub, and a first ball and a second ball engaging the first socket and the second socket to secure the shield to the needle hub;
   at least one stop piece extending radially relative to the lengthwise axis and externally of the exterior surface of the cylindrical portion, said at least one stop piece comprising a first surface and an opposed second surface and being located in a rotational path of the shield such that a base end of at least one of the sidewalls contacts the first surface of the at least one stop piece to prevent over rotation of the base end beyond a plane defined by the at least one stop piece upon contacting the first surface of the at least one stop piece in one rotational direction;
   wherein the bore of the first socket and the bore of the second socket each has an opening with a first diameter and an intermediary portion inward of the opening that increases in diameter to a second diameter larger than the first diameter.

2. The hinged shield assembly of claim 1, wherein the first surface of the at least one stop piece comprises a base element having a radially extending planar surface to abut the base end of the at least one of the sidewalls.

3. The hinged shield assembly of claim 2, further comprising a capture element extending from the base element in an axial direction to define a retention space.

4. The hinged shield assembly of claim 3, further comprising a reduced depth portion formed on at least one of the sidewalls on a side of the hinged shield assembly corresponding to the at least one stop piece.

5. The hinged shield assembly of claim 1, wherein the intermediary portion decreases in diameter to a third diameter smaller than the second diameter.

6. The hinged shield assembly of claim 3, further comprising a second stop piece comprising a first surface and an opposed second surface located in a rotational path of the shield such that a base end of a second sidewall of the sidewalls contacts the first surface of the second stop piece to prevent over rotation of the base end of the second sidewall.

7. The hinged shield assembly of claim 6, wherein the at least one of the sidewalls and the second sidewall of the sidewalls define a shield width and wherein a stop width defined by the at least one stop piece and the second stop piece is wider than the shield width or is equal to the shield width.

8. The hinged shield assembly of claim 2, wherein the at least one stop piece is located on a transverse base defining a flange, which intersects the cylindrical portion on the needle hub.

9. The hinged shield assembly of claim 8, wherein the flange has a first edge, a second edge, and a first side edge and wherein the at least one stop piece is located on the first side edge, between the first edge and the second edge.

10. The hinged shield assembly of claim 9, wherein the flange has an upper surface facing the needle, and wherein the radially extending planar surface of the base element is offset from the upper surface of the flange.

11. The hinged shield assembly of claim 3, further comprising a second stop piece and a second capture element extending from a base element of the second stop piece and wherein the two base elements define radially extending members and the two capture elements define axially extending members.

12. The hinged shield assembly of claim 11, wherein each pair of base element and capture element forms a generally "L" shape structure when viewing from an end.

13. The hinged shield assembly of claim 1, wherein each of the first ball and the second ball has a diameter that is greater than the first diameter of the opening of each of the first socket and the second socket.

14. The hinged shield assembly of claim 13, wherein each of the first ball and the second ball has at least one truncated surface.

15. The hinged shield assembly of claim 13, wherein the shield comprises both the hook extending between the sidewalls for engaging the needle or the tab for engaging the needle hub.

16. A hinged shield assembly comprising:
   a needle hub comprising a cylindrical portion with a lengthwise axis, an exterior surface and a hollow interior sized and shaped to receive a syringe tip, and a flange extending from the cylindrical portion having a first edge, a second edge, a first side edge, and a second side edge and having a first socket and a second socket located at the second edge of the flange;
   a needle extending from the needle hub and comprising a needle tip and a lengthwise axis;
   a shield comprising sidewalls with base ends including a first sidewall and a second sidewall and wherein the sidewalls partially surround the needle when the shield is in a protected position;
   a first ball located on an inner surface of the first sidewall and a second ball located on an inner surface of the second sidewall engaging the first socket and the second socket on the flange of the needle hub; and
   two stop pieces including a first stop piece located at the first side edge of the flange and a second stop piece located at the second side edge of the flange, each of the two stop pieces comprising a first surface and an opposed second surface extending radially relative to the lengthwise axis and externally of the exterior surface of the cylindrical portion, said two stop pieces being located in a rotational path of the shield such that the base end of the first sidewall and the base end of the second sidewall contact the two stop pieces to prevent over rotation of the base ends of the first and second sidewalls beyond a plane defined by the two stop pieces in one rotational direction;
   wherein a bore of the first socket and a bore of the second socket each comprises an opening with a first diameter and an intermediary portion inward of the opening that increases in diameter to a second diameter larger than the first diameter.

17. The hinged shield assembly of claim 16, wherein each of the two stop pieces has a base element and a capture element extending from the base in an axial direction to define a retention space.

18. The hinged shield assembly of claim 17, wherein at least a portion of the base end of the first sidewall and at least a portion of the base end of the second sidewall are both located in the two retention spaces.

19. The hinged shield assembly of claim 16, wherein the intermediary portion decreases in diameter to a third diameter smaller than the second diameter.

20. The hinged shield assembly of claim 18, wherein the base end of the first sidewall and the base end of the second sidewall each comprises a reduced depth portion and wherein the reduced depth portion is located in a respective retention space.

21. The hinged shield assembly of claim 16, further comprising a tab on each of the first and second sidewalls for engaging the needle hub in the protected position.

22. The hinged shield assembly of claim 21, further comprising two spaced apart notches at the first edge of the flange, and wherein the two tab of the first sidewall and the tab of the second side wall engage the two spaced apart notches.

23. The hinged shield assembly of claim 16, wherein the two stop pieces define a stop width.

24. The hinged shield assembly of claim 23, wherein the first sidewall and the second sidewall of the sidewalls define a shield width and wherein the stop width is wider than the shield width, equal to the shield width, or less than the shield width.

25. The hinged shield assembly of claim 16, wherein each of the first ball and the second ball has at least one truncated surface.

26. A method of manufacturing a hinge shield assembly comprising:
   forming a needle hub with a flange bisected by a cylindrical portion having an exterior surface and a hollow interior sized and shaped to receive a distal end of a syringe;
   forming a first hinge part with the flange, said first hinge part comprising two sockets including a first socket having a bore and a second socket having a bore, and wherein the bore of the first socket and the bore of the second socket each comprising an opening with a first diameter and an intermediary portion inward of the opening that increases in diameter to a second diameter larger than the first diameter;
   extending a needle from the needle hub, said needle comprising a needle tip and a lengthwise axis;
   forming a shield with a wall structure and a base end to at least partially surround the needle in a protected position, said shield including a second hinge part comprising two spaced apart balls;
   engaging the two spaced apart balls to the two sockets of the first hinge part to pivotably secure the shield to the needle hub; and
   forming at least one stop piece and extending the at least one stop piece from the flange radially relative to the lengthwise axis at a location externally of the exterior surface of the needle hub, the at least one stop piece comprising a first surface and an opposed second surface and being positioned in a rotational path of the shield such that the base end of the wall structure contacts the first surface of the at least one stop piece to prevent over rotation of the base end of the wall structure beyond an at rest point of the at least one stop piece in one rotational direction when the shield is in the protected position.

* * * * *